(12) United States Patent
Elliott et al.

(10) Patent No.: US 6,242,389 B1
(45) Date of Patent: *Jun. 5, 2001

(54) ETHERS

(75) Inventors: Gregory Phillip Elliott, Twickenham; Steven Ronald Wade, Chertsey, both of (GB)

(73) Assignee: BP Chemicals Limited, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/059,358

(22) Filed: Apr. 13, 1998

Related U.S. Application Data
(60) Provisional application No. 60/044,360, filed on Apr. 29, 1997.

(30) Foreign Application Priority Data

Apr. 14, 1997 (GB) .................................................. 9707496

(51) Int. Cl.$^7$ ........................................................ C09K 7/02
(52) U.S. Cl. ............................ 507/136; 568/625; 507/145
(58) Field of Search .................................. 507/136, 138, 507/145; 568/625

(56) References Cited

U.S. PATENT DOCUMENTS

| | | |
|---|---|---|
| Re. 31,163 | 3/1983 | Gardner . |
| 3,340,309 * | 9/1967 | Weipert ............................. 568/625 |
| 3,718,585 | 2/1973 | Lummus et al. . |
| 4,207,421 * | 6/1980 | Scardera et al. ..................... 568/625 |
| 4,340,766 * | 7/1982 | Klahr et al. ......................... 568/625 |
| 4,414,121 | 11/1983 | Aiello . |
| 4,536,528 | 8/1985 | George, Jr. et al. . |
| 4,941,981 * | 7/1990 | Perricone ............................. 507/136 |
| 4,963,273 | 10/1990 | Perricone et al. . |
| 5,030,365 | 7/1991 | Christensen et al. . |
| 5,120,708 | 6/1992 | Melear et al. . |
| 5,120,783 | 6/1992 | Nosu et al. . |
| 5,229,017 * | 7/1993 | Nimerick et al. .................... 507/136 |
| 5,518,996 | 5/1996 | Maroy et al. . |
| 5,557,103 | 9/1996 | Hughes et al. . |
| 5,633,220 | 5/1997 | Cawiezel et al. . |
| 5,658,859 | 8/1997 | Burba, III et al. . |
| 6,054,416 * | 4/2000 | Bland ................................. 507/136 |
| 6,063,737 * | 11/2000 | Haberman et al. ................... 507/136 |
| 6,103,671 * | 8/2000 | Dobson et al. ...................... 507/136 |

FOREIGN PATENT DOCUMENTS

| | | |
|---|---|---|
| 0 495 579 A2 | 7/1992 | (EP) . |
| 629649 A1 | 12/1994 | (EP) . |
| 670359 A1 | 9/1995 | (EP) . |
| 681017 A1 | 11/1995 | (EP) . |
| 2252993 * | 8/1992 | (GB) . |
| 2 283 036 | 4/1995 | (GB) . |
| 2 297 774 | 8/1996 | (GB) . |
| 2 297 775 | 8/1996 | (GB) . |
| 0 0706684A | 3/1995 | (JP) . |
| 147925 B2 | 1/1990 | (PL) . |
| 94739 B1 | 8/1988 | (RO) . |
| 101893 | 7/1991 | (RO) . |
| 107676 B1 | 12/1993 | (RO) . |
| 1451154 | 1/1989 | (SU) . |
| 1313860 | 5/1989 | (SU) . |
| 1720681 A1 | 3/1992 | (SU) . |
| WO 92/07919 | 5/1992 | (WO) . |
| WO 9506695 A1 | 3/1995 | (WO) . |
| WO 9607710 A1 | 3/1996 | (WO) . |
| WO 97/07183 | 2/1997 | (WO) . |

OTHER PUBLICATIONS

Quality Criteria in Selecting Glycols as Alternatives to Oil–Based Drilling Fluid Systems by R.G. Bland, Baker Hughes INTEQ, Society of Petroleum Engineers, SPE 27141, (1994).

Horizontal Well Drill–In Fluid Utilising Alcohol Ethoxylate by R.P. Jachnik and P. Green, Baker Hughes INTEQ, Society of Petroleum Engineers, SPE 28963, (1995).

SPE 2nd Inernational "Health, Safety, and Environment in Oil & Gas Production" Conference (Jakarta 1/25–27/94) Proceedings VI 399–411 (1994) (Abstract).

Trans.–Geotherm. Resour. Counc. (1979), 3 (Expanding Geotherm. Front.) 565–8 (Abstract).

\* cited by examiner

*Primary Examiner*—Philip Tucker
(74) *Attorney, Agent, or Firm*—Fay, Sharpe, Fagan, Minnich & McKee, LLP

(57) ABSTRACT

A glycol ether block copolymer for use in low potassium content aqueous drilling fluids of the formula I

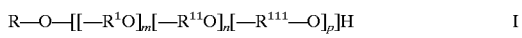

$$R-O-[[-R^1O]_m[-R^{11}O]_n[-R^{111}-O]_p]H \qquad I$$

wherein the —$R^1O$ and —$R^{11}O$ groups may be in either order attached to the R—O group, and the $R^{111}O$ group, if any is spaced from the RO group by the $R^{11}O$ group and $R^1O$ group, and is different from the group $R^{11}$ or $R^1O$ to which it is bonded directly. R is an organic group e.g. a hydrocarbyl group, $R^1$ is an ethylene group, each of $R^{11}$ and $R^{111}$, which are the same or different is a propylene, butylene ethylene group, m is 1–10 or an average of 1.0–10, while n is 1–10 or an average of 1.0–10, p is O or an average of 0.5–5 and the sum of m and n is at least 3.0.

12 Claims, No Drawings

ETHERS

This application claims benefit of provisional application 60,044,360 filed Apr. 29, 1997.

The present invention relates to ethers, in particular glycol ethers, and their uses in aqueous drilling muds.

Drilling fluids are used in the drilling of wells, such as oil or gas wells. They act as lubricant for the drilling process e.g. drilling bit, and remove the drill cuttings. The fluid is injected down the drillstring to the drill bit and removed whereupon it suspends the cuttings and carry them back to the surface, usually in the annulus between the outside of the drillstring and the well wall. At the surface, the cuttings are separated and the mud reused. The fluid is also usually weighted to increase its density in order to maintain a desired pressure down hole; the weighting can be achieved with insoluble solids such as barite or soluble solids such as alkali and alkaline earth metal salts e.g. halides.

Initially oil based fluids or muds (OBM) were used, but increasingly water based "muds" (WBM) are preferred as these can contribute less of an environmental problem than OBM. But WBM have a problem as the passage of the fluid up the outside of the drillstring can cause swelling of formation material such as clay or shale and its removal thereby enlarging the hole. To reduce this, shale inhibitors may be added to the WBM. Our EPA-495579 describes a WBM comprising a glycol or glycol ether, and a potassium salt in amount of 5–50ppb (pounds per barrel) (i.e. 14.3–143 g/l); these WBM have improved shale inhibition.

But potassium salts may have environmental disadvantages in relation to their effect on marine fauna so in some locations their level of use may be curtailed. However, we have found that replacement of the potassium chloride in the compositions of EP 495579 by other alkali or alkaline earth metal halides significantly reduces the shale inhibition activity.

Glycol ethers may now be found which can give at least as good shale inhibition effect in combination with alkali metal and alkaline earth metal halides as with potassium chloride. By this means the same base glycol ether can be used in locations allowing or not allowing potassium chloride, thereby reducing inventory costs.

The present invention provides a glycol ether block copolymer or mixture thereof of the formula I

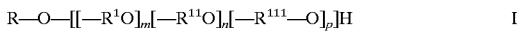

$$R-O-[[-R^1O]_m[-R^{11}O]_n[-R^{111}-O]_p]H \quad I$$

wherein the —$R^1O$ and —$R^{11}O$ groups may be in either order attached to the R—O group, and the $R^{111}$ group, if any is spaced from the RO group by the $R^{11}O$ group and $R^1O$ group, and is different from the group $R^{11}$ or $R^1O$ to which it is bonded directly, R is an organic group e.g. a hydrocarbyl group, $R^1$ is an ethylene group, each of $R^{11}$ and $R^{111}$, which are the same or different is a propylene or butylene group or $R^{111}$ may be an ethylene group, in is 1.0–10 or preferably is an average of 1.0–10, while n is 1.0–10 or preferably is an average of 1.0–10, p is 0 or an average of 0.5–5 and the sum of in and n is at least 3.0.

The group R may be an organic group of 1–12 carbons, in particular an organic hydrocarbyl group, especially an alkyl, group e.g. of 1–8 or 2–6 especially 1–4 carbons, an alkenyl group e.g. of 2–8 carbons, a cycloalkyl group e.g. of 5–7 carbons, an aryl group e.g. of 6–9 carbons, or aralkyl group e.g. of 7–10 carbons. The alkyl and alkenyl groups may be branched but are preferably linear.

Examples of the alkyl group are methyl, ethyl, propyl, isopropyl, n-butyl, isobutyl, sec butyl, n-amyl, n-hexyl or noctyl while examples of the alkenyl group are vinyl, allyl and crotonyl. Examples of cyclo alkyl are cyclopentyl and cyclohexyl, example of aryl are phenyl, o-, m- or p- tolyl and xylyl, and examples of aralkyl are benzyl and 2-phenylethyl. The group $R^1$ is an 1,2-ethylene group. The group $R^{11}$ or $R^{111}$ may be a 1,3-propylene or 1,2-propylene (which is preferred) or 1,4-butylene or 1,2-butylene (i.e. 2-ethyl-1,2-ethylene or 1,3-butylene), while $R^{111}$ may also be a 1,2-ethylene group.

In the block copolymers of formula 1 there are at least one $R^1O$ group and at least one $R^{11}O$ group, and a totality of at least 3 $R^1O$ and $R^{11}O$ groups; thus there may be a block of at least 2 $R^1O$ (or $R^{11}o$) groups joined to at least 1 $R^{11}O$ (or $R^1O$) groups respectively, preferably a block of at least 2 $R^{11}O$ (or $R^1O$) groups. Thus in formula 1, $(R^1O)^m$ preferably denotes a block of $R^1O$ groups bonded together, or (but preferably and) $(R^{11}O)_n$ denotes a block of $R^{1111}O$ groups bonded together.

In the copolymer, m is (or in the mixture thereof m is an average of) 1.0–10 e.g. 2.0–10, such as 2.5–5 or 2.5–4 especially 3–3.5. Most preferably the average m is derived from mixtures of individual copolymers, at least one of which preferably the majority of which and especially substantially all of which contain an integer value of m in the range 1–10. n is (or in the mixture thereof n is an average of) 1.0–10 e.g. 2–10 or 2–8 such as 2–6. Most preferably the average n is derived from mixtures of individual copolymers, at least one of which preferably the majority of which and especially substantially all of which contain an integer value of n in the range 1–10. p is 0 or an average of 0.5–5.0. The ratio ofin to n may be 0.2–5:1, but is preferably 0.3–3:1 such as 0.4–2.4:1 especially 0.5–1.5:1.

The sum of m and n, or m, n and p (and especially the sum of the average m and average n, or sum of average m, average n and average p) may be 3–15, in particular 3–12, especially an average of 4–12 such as 4–10 or 5–8. The average molecular weight of the glycol ether may be 200–900, such as 250–600. The cloud point of the glycol ether in 3% (by weight) solution in distilled water, is usually more than 35° C. or 40° C. e.g. 40–100° C.

Particularly preferred are glycol ethers II of formula I with R as linear alkyl of 3–5 carbons especially 3 or 4, $R^1O$ bonded directly to RO—, $R^{11}$ as 1,2-propylene m as 2.5–4, e.g. 3–3.5, p as 0 and n as 2.0–6.0, such as 2.0–2.8 or especially 2.8–5.0 or 3.8–5.0. Preferred average molecular weights for said glycol ethers II are 300–500 such as 300–360 or 360–480 especially 420–480, while preferred values for m:n are 1.5–0.5:1, such as 1.5–1.1:1 or especially 1.1–0.6:1 such as 0.85–0.6:1, and preferably the sum of m and n is 5–8, in particular 5–6 or 6–8, especially 7–8.

The glycol ether may be present as a single molecule but is usually as a mixture of glycol ethers, especially with one particular R group and a range of numbers of one of the groups $R^1O$ or $R^{11}O$ which is spaced from the RO group by the other of the $R^{11}o$ and $R^1O$. That other group may be present in a substantially single number e.g. 3 or 4, or may be itself in a range of numbers such as 2.5–6. The glycol ethers may be made (according to a further aspect of the invention) by stepwise reaction of a hydroxylic compound of formula ROH, with an alkylene oxide of 2–4 carbons of formula $R^1O$ or $R^{11}O$, e.g. ethylene oxide, and then after reaction is substantially complete e.g. for the number of $R^1O$ (or $R^{11}O$) units to be reacted with ROH, then the reaction product is reacted further with a second different alkylene oxide of 2–4 carbon atoms of formula $R^{11}O$ or $R^1O$ respectively e.g. propylene oxide, again until reaction is substantially complete. The alkylene oxide reactions are preferably performed in the presence of a catalyst e.g. a basic catalyst such as an alkali metal hydroxide, alkoxide (e.g. of 1–6 carbons such as methoxide or ethoxide) or carboxylate (e.g. alkanoate of 1–6 carbons such as formate or acetate) especially in weight amount of 0.01–10% by weight of the hydroxylic compound ROH such as 0.05–1%, or in weight amount of 0.01–5% by weight of the total of hydroxylic compound and alkylene oxide The stepwise reaction tends to produce glycol ethers with a wide range of numbers of —$R^1O$— and —$R^{11}O$ groups.

Alternatively according to a process which is a second aspect of the invention, the hydroxylic compound ROH may be reacted with the first alkylene oxide to give a range of products with for example 1–4 alkyleneoxy units, and then by distillation the products with 1, or 1,2 or 1,2,3 units may be predominantly separated to leave a cut of reduced range distribution e.g. 3-4. This glycol ether cut e.g. of formula R—O—$[R^1O]_m$H where m is 3–4 especially 3.0–3.5, may then be reacted with the second alkylene oxide in the manner described above. In both steps a catalyst e.g. as mentioned may be used.

If desired the cut of reduced range distribution may be alkenoxylated in a different reactor from the first step, and may have been transported there from a far location.

The block copolymers of the invention may be made by reaction of one of (i) an olefin oxide $R^{11}O$ and (ii) an olefin oxide $R^1O$ with one of (i) R—O—$[R^1O]_m$H III and (ii) R—O—$[R^{11}O]_n$H (IV) respectively, and then optionally reaction of the block copolymer product with an olefin oxide $R^{111}O$. The glycol ethers of formula III and IV may be made by reaction of the hydroxylic compound ROH with an olefin oxide of formula either $R^1O$ or $R^{11}O$ respectively, followed optionally by at least partial separation of glycol ethers with in or n values of 1, or preferably 1 and 2. The present invention provides a block copolymer (especially a mixture thereof) obtained by or obtainable by the above processes.

Before use the glycol ether, or especially glycol ether mixture may be purified e.g. by distillation to remove volatiles such as unreacted alcohol and alkylene oxide and/or volatile catalyst (if any).

The present invention also provides a composition, comprising a glycol ether of this invention and water soluble alkali metal or alkaline earth metal salt, in particular one other than potassium chloride. The salt may be of lithium sodium, potassium or caesium, especially sodium, or of magnesium or calcium, especially calcium, and its associated anion, which may be mono or divalent, may be a halide with atomic number above 20, such as chloride or bromide, or nitrate or for alkali metals, a carbonate, bicarbonate, sulphate, bisulphate or carboxylate especially of 1–8 e.g. 1–4 carbon atoms e.g. formate or acetate or hydroxycarboxylate e.g. glycollate or citrate. Sodium chloride, calcium chloride, caesium formate and caesium acetate are preferred. The salt usually has a solubility in water at 25° C. of at least 1% e.g. at least 10% (by weight) in the composition. The weight ratio of the glycol ether to the salt may be 1:0.1–20 in particular 1:0.5–5.0.

The present invention also provides an aqueous drilling fluid which comprises water and, at least one glycol ether of the invention and preferably at least one of said water soluble alkali metal or alkaline earth metal salts, e.g. a composition of the invention. The water may be fresh, salt, sea or formation water and may contain up to 1000ppm or preferably up to 500 ppm of potassium, as well as variable amounts of sodium, magnesium and calcium and have a total of up 50,000 ppm of salts (excluding the added alkali metal or alkaline earth metal salt) in particular up to 40,000 ppm salts (on the same basis). Thus in one aspect the invention provides an aqueous drilling fluid comprising water and at least one glycol ether of the invention, the total salts concentration (including any added salt) being up to 50,000 ppm especially up to 20,000 ppm or 10,000 ppm in particular at least 100 ppm (e.g. when the drilling fluid is from freshwater), or 20,000–50,000 ppm (e.g. when the drilling fluid is from salt, sea or forination water. Preferably however the drilling fluid contains added salt.

The aqueous drilling fluid may contain 0.5–50% v/v of the glycol ether and 2–50ppb (pounds per barrel) (5.7–143g/1) of the salt, in particular 1–20% v/v of the glycol ether. In particular the drilling fluid may contain less than 14.2 g/l potassium, preferably less than 5 g/l and especially less than 1 g/l potassium. The aqueous drilling fluid preferably contains 5–20 ppb (14.3–57.2 g/l) of salt especially sodium chloride or calcium chloride, or alternatively 20–40 ppb (57.2–114.4 g/l) of salt especially sodium or calcium chlorides, both in particular with 1–5% w/v of the glycol ether of formula I especially of formula II.

The aqueous drilling fluid may also contain at least one conventional additive for aqueous drilling fluid, e.g. fluid loss control agent such as starch or a cellulose derivative e.g. carboxymethyl cellulose in amount e.g. of 1–5 ppb, insoluble weighting agent e.g. barite, haematite or galena in amount e.g. of 1–200 ppb, viscosifier e.g. xanthan gum in amount e.g. of 1–3 ppb, and pH control agents such as sodium hydroxide. The specific gravity of the drilling fluid may be 1.0–1.25 e.g. 1.01–1.10 excluding insoluble weighting agents (if any). The pH of the drilling fluid may be of 7–13.

The present invention also provides a method of drilling which comprises passing a drilling fluid down hole to a drilling means in a formation, said drilling means producing loose formation solids, and then returning said fluid carrying said solids in contact with the hole well to a formation solids collection point, wherein the drilling fluid is according to the invention.

The present invention also provides a method of inhibiting the swelling of shale during drilling operations, which comprises contacting the shale with a drilling fluid of the invention.

The invention is illustrated in the following Examples in which the starting glycol ether was a mixture of ethenoxylated n-butanols with a molar average of butyl to ethyleneoxy unit of 1:3.19 made by reaction of butanol with ethylene oxide in the presence of a basic catalyst, followed by vacuum distillation of the mono butyl ethers of mono and di ethylene glycol to leave residue of crude mono butyl triethylene glycol, which was then itself distilled to give the starting glycol ether.

Glycol Ether Preparation Ex. 1–5

175 g of the mixture of starting glycol ethers with an average Bu(EO) ratio of 1:3.19, 144.7 g of propylene oxide and 0.32 g of sodium hydroxide (0. 1% wt) were added to a stirred steel autoclave. The autoclave was purged with dry nitrogen, and pressurised to approximately 10 Barg with nitrogen. The temperature was then raised to 120° C., and the pressure increased to 30 Barg by application of further nitrogen. After 16 hours under these conditions with stirring, the autoclave was allowed to cool to approximately 40° C., and the pressure reduced to atmospheric. Dry nitrogen was passed through the autoclave for at least two hours to purge out any unreacted propylene oxide. Yield of recovered product (Ex.2) was 316.3 g, 98.8% wt basis. The same procedure was used in each of the other Examples (1 and 3–5) but with variations in the amount of propylene oxide.

| Compound | Average Formula (based on starting stoichiometry) |
|---|---|
| 1 | $BuO(EO)_{3.19}(PO)_{2.5}H$ |
| 2 | $BuO(EO)_{3.19}(PO)_{3.0}H$ |
| 3 | $BuO(EO)_{3.19}(PO)_{3.5}H$ |
| 4 | $BuO(EO)_{3.19}(PO)_{4.0}H$ |
| 5 | $BuO(EO)_{3.19}(PO)_{4.5}H$ |

Spectroscopic analysis by nmr and mass spectroscopy confirmed the above block copolymer structures.

Shale Inhibition Tests

In each experiment the procedure involved making up various water and glycol ether mixtures, adding a known amount of crushed and sieved dispersive clay (1–2 mm fraction) and rolling the resulting mixture at room temperature and 25 rpm for 16 hours. At the end of this time, the non dispersed clay fraction (>0.5 mm) was recovered, dried at 100° C. for 16 hr, and weighed. The water content of a sample of the original 1–2 mm clay fraction was determined from the weight in drying at 100° C. over 16hr.

The tests were carried out on London clay, a Tertiary clay rich in swelling minerals and representative of a North Sea gumbo, Shale may be defined as a fine grained sedimentary rock composed of consolidated silt and clay or mud, and Tests on clay samples are equivalent to tests on shales, a higher recovery of undispersed clay denoting less clay dispersion and therefore greater shale inhibition.

In each case 3.0 g of the glycol ether of Ex. 1–5 or a commercial butyl glycol ether random ethylene oxide/propylene copolymer of average formula $BuO (EO)_5(PO)_5H$ (Compound A) was mixed with 97 g of the appropriate aqueous solution, and the % of the recovered undispersed clay measured.

The aqueous solutions were (a) fresh water with a total of at least 100 ppm dissolved salts, (b) sea water with a total of 3.5% dissolved salts and (c) a calcium chloride brine, containing 1oppb (28.6 g/l) of calcium chloride added to the sea water. In each the shale inhibitor experiments were repeated three times (i.e. 4 experiments in total) and an average result calculated. The results were as follows.

| | | % shale recovery | | |
|---|---|---|---|---|
| Example | Compound | fresh water | sea water | $CaCl_2$ soln. 10 ppb |
| Comparative example 1 | None | 0.7 | 1.0 | 1.1 |
| Comparative example 2 | A | 9.5 | 50.4 | 30.1 |
| 6 | 1 | 24.3 | 59.3 | 77.6 |
| 7 | 2 | 37.1 | 67.1 | 81.7 |
| 8 | 3 | 43.7 | 71.1 | 81.6 |
| 9 | 4 | 54.9 | 76.8 | 85.6 |
| 10 | 5 | 58.7 | 77.7 | 87.2 |

We claim:

1. An aqueous drilling fluid which comprises a composition comprising a mixture of glycol ether block copolymer wherein said mixture has an average formula I $$R-O-[[-R^1O]_m[-R^{11}O]_n[-R^{111}O]_p]H \qquad I$$

wherein either the $-R^1O$ or the $-R^{11}O$ groups are directly bonded to the R—O group, and the $R^{111}O$ group is spaced from the RO group by the $R^{11}O$ group and the $R^1O$ group, and is different from the group $R^{11}O$ or $R^1O$ group to which it is bonded directly, R is an organic group, $R^1$ is an ethylene group, $R^{11}$ is selected from the group consisting of a propylene and butylene groups, $R^{111}$ is selected from the group consisting of an ethylene, propylene and butylene groups, m is an average of 1.0–10, n is an average of 1.0–10, p is either 0 or an average of 0.5–5.0, and the sum of m and n is at least 3.0, a water soluble calcium salt and water.

2. A fluid according to claim 1 having a salt content of at least 100 ppm.

3. A fluid according to claim 1 comprising 0.5–50% v/v of the glycol ether and 2–50 ppb (pounds per barrel) (5.7–143 g/l ) of the salt.

4. A fluid according to claim 1 comprising less than 14.2 g/l of potassium.

5. A fluid according to claim 3 comprising less than 14.2 g/l of potassium.

6. An aqueous drilling fluid according to claim 1 comprising at least one conventional additive for aqueous drilling fluid.

7. A method of drilling which comprises passing a drilling fluid down hole to a drilling means in a formation, said drilling means producing loose formation solids, and then returning said fluid carrying said solids in contact with the hole well to a formation solids collection point, wherein the drilling fluid comprises a composition comprising a mixture of ether block copolymers wherein said mixture has an average formula I $$R-O-[[-R^1O]_m[-R^{11}O]_n[-R^{111}O]_p]H \qquad I$$

Wherein either the $-R^1O$ or the $-R^{11}O$ groups are directly bonded to the R—O group, and the $R^{111}O$ group is spaced from the RO group by the $R^{11}O$ group and the $R^1O$ group, and is different from the group $R^{11}O$ or $R^1O$ to which it is bonded directly, R is an organic group, $R^1$ is an ethylene group, $R^{11}$ is selected from the group consisting of a propylene and butylene groups, $R^{111}$ is selected from the group consisting of an ethylene, propylene and butylene groups, m is an average of 1.0–10, n is an average of 1.0–10, p is either 0 or an average of 0.5–5.0 and the sum of m and n is at least 3.0, a water soluble calcium salt and water.

8. A method of inhibiting the swelling of shale during drilling operation, which comprises contacting the shale with an aqueous drilling fluid which comprises a composition comprising a mixture of ether block copolymers wherein said mixture has an average formula I $$R-O-[[-R^1O]_m[-R^{11}O]_n[-R^{111}O]_p]H \qquad I$$

Wherein either the $-R^1O$ or the $-R^{11}O$ groups are directly bonded to the R—O group, and the $R^1O$ group is spaced from the RO group by the $R^{11}$ group and $R^1O$ group, and is different from the group $R^{11}O$ or $R^1O$ to which it is bonded directly, R is an organic group, $R^1$ is an ethylene group, $R^{11}$ is selected from the group consisting of a propylene and butylene groups, $R^{111}$ is selected from the group consisting of an ethylene, propylene, and butylene groups, m is an average of 1.0–10, n is an average of 1.0–10, p is either 0 or an average of 0.5–5.0, and the sum of m and n is at least 3.0, a water soluble calcium salt and water.

9. A composition comprising a mixture of glycol ether block copolymers wherein said mixture has an average formula I $$R-O-[[-R^1O]_m[-R^{11}O]_n[-R^{111}O]_p]H \qquad I$$

Wherein R is an organic hydrocarbyl group of I to 7 carbons, either the $-R^1O$ or the $-R^{11}O$ groups are directly bonded to the R—O groups, and the $R^{111}O$ group is spaced from the RO group by the $R^{11}O$ or $R^1O$ group, and is different from the group $R^{11}O$ or $R^1O$ group to which it is bonded directly, $R^1$ is an ethylene group, $R^{11}$ is selected from the group consisting of a propylene and butylene groups, $R^{111}$ is selected from the group consisting of an ethylene, propylene and butylene groups, m is an average of 1.0–10, n is an average of 1.0–10, p is either 0 or an average of 0.5–5.0, and the sum of m and n is at least 3.0 and a water soluble calcium salt.

10. A composition according to claim 9 wherein the weight ratio of the glycol ether to salt is 1:0.1–20.

11. A composition according to claim 9 wherein the salt is calcium chloride.

12. A composition according to claim 9 wherein R comprises 1–4 carbons.

* * * * *